(12) United States Patent
Brcka et al.

(10) Patent No.: US 8,916,055 B2
(45) Date of Patent: Dec. 23, 2014

(54) METHOD AND DEVICE FOR CONTROLLING PATTERN AND STRUCTURE FORMATION BY AN ELECTRIC FIELD

(75) Inventors: Jozef Brcka, Austin, TX (US); Jacques Faguet, Austin, TX (US); Eric M. Lee, Austin, TX (US); Hongyu Yue, Plano, TX (US)

(73) Assignee: Tokyo Electron Limited, Tokyo (JP)

( * ) Notice: Subject to any disclaimer, the term of this patent is extended or adjusted under 35 U.S.C. 154(b) by 0 days.

(21) Appl. No.: 13/823,690

(22) PCT Filed: Jul. 31, 2012

(86) PCT No.: PCT/US2012/049040
§ 371 (c)(1),
(2), (4) Date: May 8, 2013

(87) PCT Pub. No.: WO2013/019810
PCT Pub. Date: Feb. 7, 2013

(65) Prior Publication Data
US 2013/0217210 A1  Aug. 22, 2013

Related U.S. Application Data

(60) Provisional application No. 61/514,461, filed on Aug. 2, 2011, provisional application No. 61/664,690, filed on Jun. 26, 2012.

(51) Int. Cl.
*G01R 31/00* (2006.01)
*H01L 21/326* (2006.01)
(Continued)

(52) U.S. Cl.
CPC .......... *H01L 21/67011* (2013.01); *B03C 5/005* (2013.01); *H01J 37/32009* (2013.01);
(Continued)

(58) Field of Classification Search
CPC ... H01J 37/32697; B03C 5/005; B03C 5/026; H01L 21/02612; H01L 21/67011
USPC ............. 216/59, 61; 427/248.1, 585; 438/466
See application file for complete search history.

(56) References Cited

U.S. PATENT DOCUMENTS 7,323,096 B2  1/2008  Yoshida et al.
(Continued)

FOREIGN PATENT DOCUMENTS

| DE | 10 2006 023 238 A1 | 11/2007 |
| TW | 200300464 | 6/2003 |
| WO | 2007116406 A1 | 10/2007 |

OTHER PUBLICATIONS

Taiwan Intellectual Property Office, Examination Opinion issued in related TW Patent Application No. 101128013, issued Aug. 25, 2014, with English Translation, 15 pp.

(Continued)

*Primary Examiner* — Shamim Ahmed
(74) *Attorney, Agent, or Firm* — Wood, Herron & Evans, LLP

(57) ABSTRACT

A processing method and apparatus uses at least one electric field applicator (34) biased to produce a spatial-temporal electric field to affect a processing medium (26), suspended nano-objects (28) or the substrate (30) in processing, interacting with the dipole properties of the medium (26) or particles to construct structure on the substrate (30). The apparatus may include a magnetic field, an acoustic field, an optical force, or other generation device. The processing may affect selective localized layers on the substrate (30) or may control orientation of particles in the layers, control movement of dielectrophoretic particles or media, or cause suspended particles of different properties to follow different paths in the processing medium (26). Depositing or modifying a layer on the substrate (30) may be carried out. Further, the processing medium (26) and electrical bias may be selected to prepare at least one layer on the substrate (30) for bonding the substrate (30) to a second substrate, or to deposit carbon nanotubes (CNTs) with a controlled orientation on the substrate.

35 Claims, 15 Drawing Sheets

(51) Int. Cl.
- H01L 21/67 (2006.01)
- B03C 5/00 (2006.01)
- H01J 37/32 (2006.01)
- C12M 3/00 (2006.01)
- C12M 1/26 (2006.01)
- B03C 5/02 (2006.01)
- A61F 2/00 (2006.01)
- H01L 21/02 (2006.01)

(52) U.S. Cl.
CPC .......... *H01J 37/32697* (2013.01); *C12M 21/08* (2013.01); *C12M 33/00* (2013.01); *B03C 5/026* (2013.01); *A61F 2/00* (2013.01); *H01L 21/02612* (2013.01)
USPC ............ 216/61; 216/59; 438/466; 427/248.1; 427/585

(56) References Cited

U.S. PATENT DOCUMENTS

| | | |
|---|---|---|
| 7,744,737 B1 | 6/2010 | James et al. |
| 7,857,952 B2 | 12/2010 | Yoshida et al. |
| 2004/0058423 A1 | 3/2004 | Albritton et al. |
| 2004/0096430 A1 | 5/2004 | Bauer |
| 2005/0032204 A1 | 2/2005 | Rodgers et al. |
| 2008/0138797 A1 | 6/2008 | Hunt et al. |
| 2009/0220865 A1* | 9/2009 | Ouye ................. 430/5 |
| 2009/0314644 A1 | 12/2009 | Golan et al. |
| 2010/0203742 A1* | 8/2010 | Borden et al. ........... 438/783 |
| 2011/0079513 A1 | 4/2011 | Stelzle et al. |
| 2012/0208339 A1* | 8/2012 | Cheng et al. ............ 438/382 |

OTHER PUBLICATIONS

European Patent Office, International Search Report and Written Opinion in corresponding PCT Application No. PCT/US2012/049040, mailed Mar. 6, 2013, 12 pp.

European Patent Office, International Search Report and Written Opinion in corresponding International Application No. PCT/US2012/049056, mailed May 17, 2013, 11 pp.

ESPACENET, EPO English Machine Translation of Application No. DE 10 2006 023 238 (A1), Published Nov. 22, 2007, http://worldwide.espacenet.com, retrieved Jul. 19, 2013, 12 pp.

Chen et al., "Aligning single-wall carbon nanotubes with an alternating-current electric field," Appl. Phys. Lett. 78 (23):3714-3716, 2001.

Dimaki et al., "Dielectrophoresis of carbon nanotubes using microelectrodes: a numerical study," Nanotechnology, 15:1095-1102, 2004.

Ho et al., "Rapid heterogeneous liver-cell on-chip patterning via the enhanced field-induced dielectrophoresis trap," Lab Chip, 6:724-734, 2006.

* cited by examiner

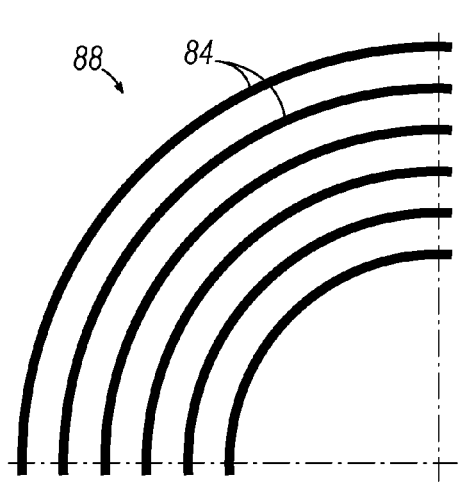
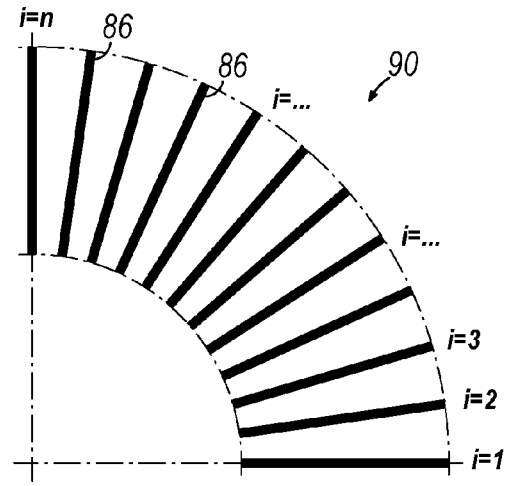
FIG. 6A  FIG. 6B
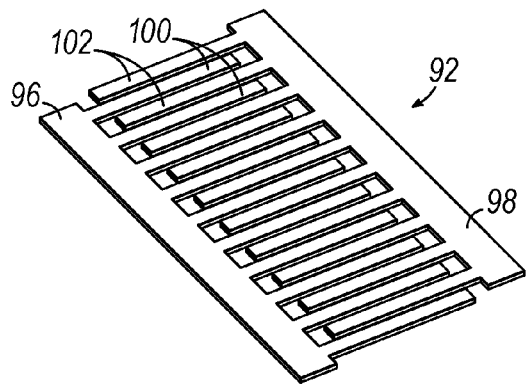
FIG. 7
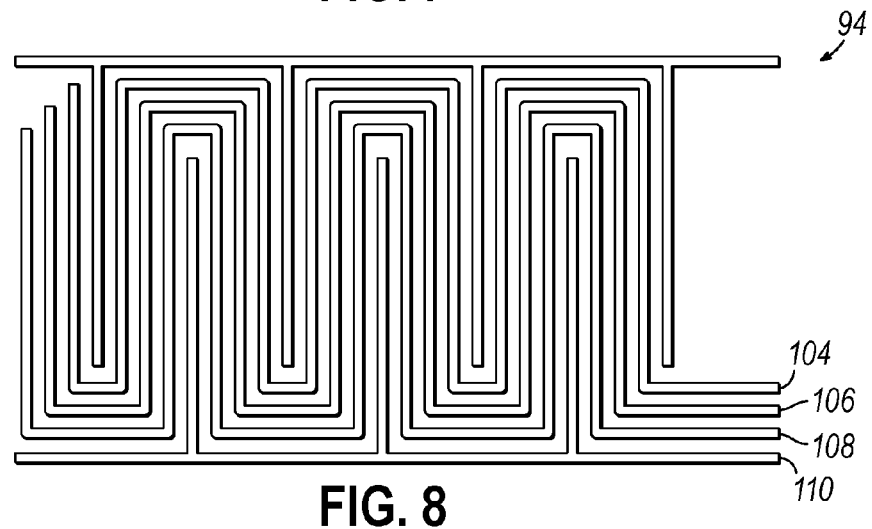
FIG. 8

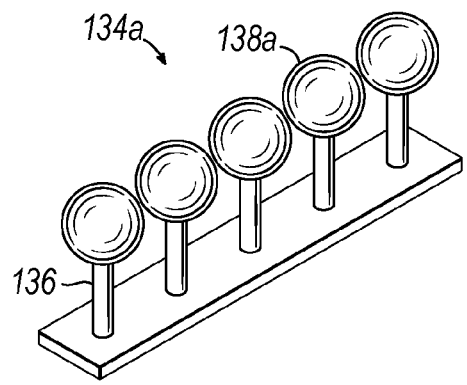 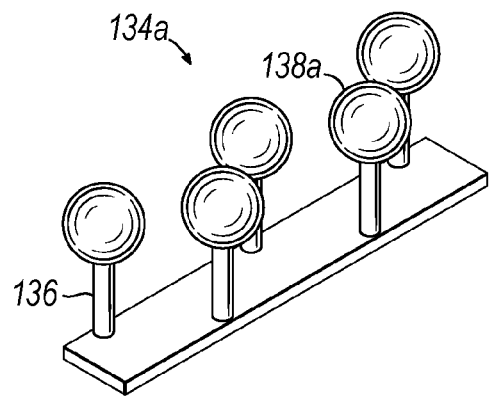
FIG. 13A  FIG. 13B
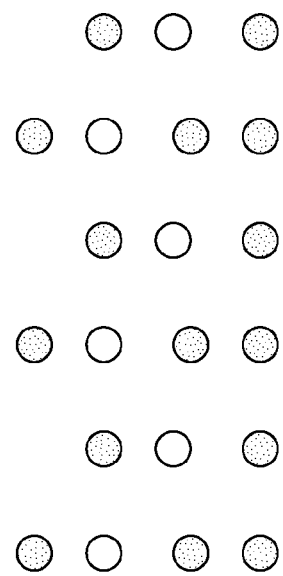
FIG. 14

METHOD AND DEVICE FOR CONTROLLING PATTERN AND STRUCTURE FORMATION BY AN ELECTRIC FIELD

CROSS-REFERENCE TO RELATED APPLICATIONS

This application is a national phase application of International Application Serial No. PCT/US12/49040, filed Jul. 31, 2012, which claims the benefit of and priority to prior filed Provisional Application Ser. No. 61/514,461, filed Aug. 2, 2011, and Provisional Application Ser. No. 61/664,690, filed Jun. 26, 2012, the disclosure of each is expressly incorporated herein by reference, in its entirety. This application is also related to commonly assigned International Application Serial No. PCT/US12/49056 entitled SYSTEM AND METHOD FOR TISSUE CONSTRUCTION USING AN ELECTRIC FIELD APPLICATOR filed Jul. 31, 2012 by the inventor hereof, hereby expressly incorporated herein by reference.

FIELD OF THE INVENTION

This invention relates to the formation of patterns or structures, particularly by film formation on substrates, utilizing nanometer to micron scale objects. More particularly the invention relates to such formation of patterns or structures by the manipulation of such objects and to the use of electric field applicators and to devices and methods utilizing electric field applicators to manipulate nano-to-micrometer scale objects.

BACKGROUND OF THE INVENTION

Developments in nanotechnology, the manipulation of matter on the scale of 1 nm to 100 nm, have yielded materials and devices with applicability in medicine, electronics, and energy production, to name a few. Conventionally, there have been two approaches to continued developments in nanotechnology: bottom-up and top-down. Bottom-up approaches arrange nano-components into complex assemblies and have been useful in molecular assembly, atomic force microscopy, and DNA engineering. Top-down approaches create smaller devices by utilizing the influences of larger devices. For example, atomic layer deposition ("ALD") is a process by which semiconductor elements are built at atomic-layer scales.

To further capitalize on the benefits of nanotechnology, the ability to manipulate, activate, measure, characterize, and quantify nano-objects must be controlled with precision and at high-throughput. The human-like, individual interactions of the conventional bottom-up approaches are not suitably efficient for scaling up to mass production.

However, sufficient control over nano-objects using top-down approaches must include electrodes of similar scale that are also configured to generate forces sufficient to manipulate the nano-objects. Due to the complexities of physics, geometrical factors, and the specificity needed for particular applications, electrode design and processing systems are not straight forward. Therefore, there remains a need to provide specific control in spatially enhancing and/or suppressing interactions between generated fields and nano-objects. Furthermore, it would be beneficial for semiconductor technology to merge with bioelectronics fabrication to develop novel approaches to the manipulation of nano-objects.

In addition, in semiconductor processing, electric field control has been effective in manipulating the motion of ions or other charged particles, as disclosed in U.S. Pat. No. 7,867,409. Systems employing media or particles that only exhibit dielectrophoretic properties in the presence of electric fields are not well developed. Accordingly, there is a need to better control nano and other small objects in a processing medium during processing structures on substrates.

SUMMARY OF THE INVENTION

The present invention overcomes the foregoing problems and other shortcomings and drawbacks of the known, conventional nano-object manipulation and control. While the present invention will be described in connection with certain embodiments, it will be understood that the present invention is not limited to these embodiments. To the contrary, this invention includes all alternatives, modifications, and equivalents as may be included within the scope of the present invention. These alternatives and modifications include, for example, extending the application novel nano-object manipulation and control solutions and their application to semiconductor technology to micro-object manipulation and control and to bioelectronic fabrication and other applications.

In accordance with the present invention, the processing of a film upon a substrate or the other formation or modification of patterns or objects with the use of micro-or-nano size objects is enhanced by the application and control of temporally and spatially controlled electric fields.

According to certain embodiments of the invention, a processing apparatus is provided having a processing chamber configured to receive a processing medium having dipole properties that are subject to being affected by an electric field while processing a substrate; and a substrate holder for holding a substrate to be processed within the chamber. The apparatus is provided with at least one electric field applicator that is operable to expose the substrate during processing to a spatial-temporal electric field that is capable of affecting the processing medium or the substrate when the electric field applicator is electrically energized by an electrical bias selected to interact with the dipole properties of the medium or particles therein. The electric field applicators may be addressable by a controller and may be interchangeable. A distribution coupling unit is provided that is operable to couple a time-varying electrical bias to the at least one electric field applicator to thereby energize the electric field applicator in a way that will affect the medium or the particles. A controller is provided to operate the apparatus to control temporal and spatial characteristics of the applied electric field to affect the processing medium to achieve a processing effect on the substrate. The processing medium may be a gas or a liquid. An electric field applicator may be located outside the processing chamber and transmit the electric field to the substrate, or be located inside the processing chamber, such as adjacent the substrate. The electric field processing apparatus may be of a size substantially equal to the size of the substrate or of a size smaller than the size of the substrate and configured to be scanned across the substrate. Where substantially equal to the size of the substrate, it may be a stationary part of the apparatus and activated and addressed by grid structure or other logic circuitry according to an appropriate spatial and time-domain algorithm. Where smaller, it may be controlled by some such algorithm as well as motion with respect to the substrate.

According to certain embodiments of the invention, the electric field processing may include an irradiation source, such as, for example, a microwave radiation source, an ultraviolet radiation source, or an infrared radiation source. Further, the electrical bias may include a DC potential component, an AC or RF potential, a switched DC potential, another time varying waveform, or a combination thereof. The potential may be applied to the electric field by a distribution coupling unit through direct electrical contact, or by capacitive or inductive coupling. The apparatus may include a magnetic field generator, an acoustic field generator, or an optical force generation device to further influence the nano-objects.

In certain embodiments of the processing apparatus, the processing medium and electrical bias may be configured for selective localized deposition of layers on the substrate. In a specific embodiment, the processing medium and electrical bias are configured for deposition of carbon nanotubes (CNTs) with a controlled orientation. The time-varying electrical bias in many embodiments varies at less than 10,000 Hz, and typically at less than 1,000 Hz.

According to certain methods of the present invention, electric field processing of a substrate is carried out with a processing apparatus by supporting a substrate to be processed in a chamber, introducing a processing medium into the chamber which may also have particles carried by the medium, with the medium and particles possessing a dipole configuration when subjected to an appropriate electrical field. Then, a time-varying electrical bias is applied to at least one electric field applicator to create the electric field appropriate to affect the processing medium or particles therein in a desired way in the vicinity of or at the surface of the substrate. Then the substrate is processed with the affected processing medium and/or particles. The processing may include constructing one or more layers on the substrate, for example, or controlling the movement of suspended dielectrophoretic particles in the medium or onto the substrate, for example, particularly where the substrate is a semiconductor wafer and the process is etching material on the substrate or depositing a material onto the substrate. In some embodiments, the motion of suspended particles may be affected to cause suspended particles of different properties to follow different paths in the processing medium, which may be used to cause the suspended particles to be sorted. Further, the suspended particles may be bioagents, and the motion of suspended particles may be controlled in part by applying a static or time-varying electrical bias so as to deposit the suspended particles at predetermined locations on the substrate.

In some embodiments, irradiating of the substrate may be carried out, for example, with microwave radiation, ultraviolet radiation, or infrared radiation sources. Depositing or modifying a layer on the substrate may also be carried out, such as with filament-assisted chemical vapor deposition (FACVD) or initiated chemical vapor deposition (iCVD). Further, the processing medium and electrical bias may be selected to prepare at least one layer on the substrate for bonding the substrate to a second substrate, or, may be selected to deposit carbon nanotubes (CNTs) with a controlled orientation, on the substrate. In some embodiments, the processing medium and electrical bias may be selected to affect the structure, or orientation, or both, of a first deposited layer on the substrate, and may do so differently for different layers on the substrate.

These and other embodiments of the invention may be readily apparent from the following detailed description in which:

BRIEF DESCRIPTION OF THE DRAWINGS

The accompanying drawings, which are incorporated in and constitute a part of this specification, illustrate embodiments of the present invention and, together with a general description of the invention given above, and the detailed description given below, serve to explain the invention.

FIGS. 5A, 5B, 6A, 6B, and 7-9 illustrate grid members suitable for the grid member of the process chamber of FIG. 1 and according to various embodiments of the present invention.

FIGS. 12A-13B illustrate electrodes in periodic arrays in accordance with various embodiments of the present invention.

FIG. 14 is a schematic illustration of groups of electrodes from FIG. 13A illustrated in a grid-like pattern for providing electric field zones as shown in FIG. 3A.

DETAILED DESCRIPTION

Figure 1:
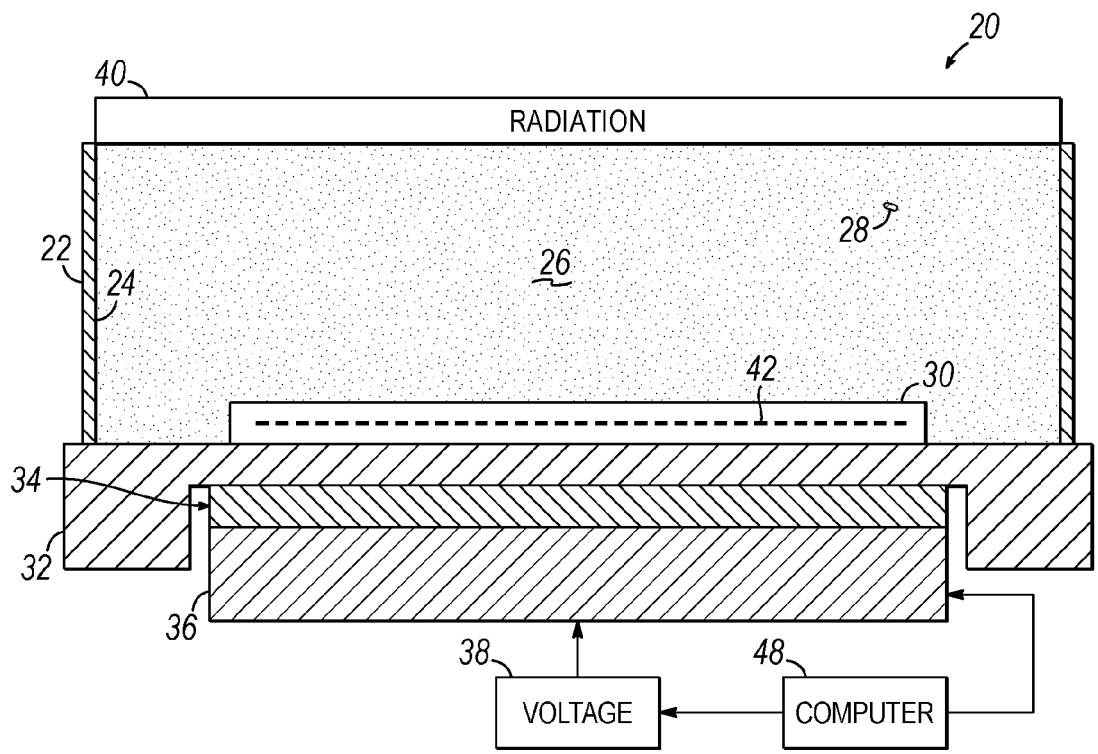
FIG. 1 is a schematic cross-sectional view of a processing chamber having an electric field applicator in accordance with one embodiment of the apparatus of the present invention.

With reference now to the figures, and in particular to FIG. 1, a processing chamber 20 suitable for use with one or more embodiments of the present invention is shown and described in detail. The processing chamber 20 includes a chamber wall 22 enclosing a processing space 24, which may be filled with a processing medium 26 including one or more fluids, solutes, and/or dispersants. Exemplary processing medium 26 may include atmospheric gas, reactive gas, low pressure vapor near vacuum, colloidal organic media, hydrogels, resin, organic solvent, water, alcohol, and so forth, and will be dependent on the particular application for which the processing chamber 20 is being used. The size of the processing space 24 is likewise dependent on the particular application and will vary accordingly; however, a processing space 24 having a volume ranging from about 0.1 L to several liters may be typical.

Figure 16A:
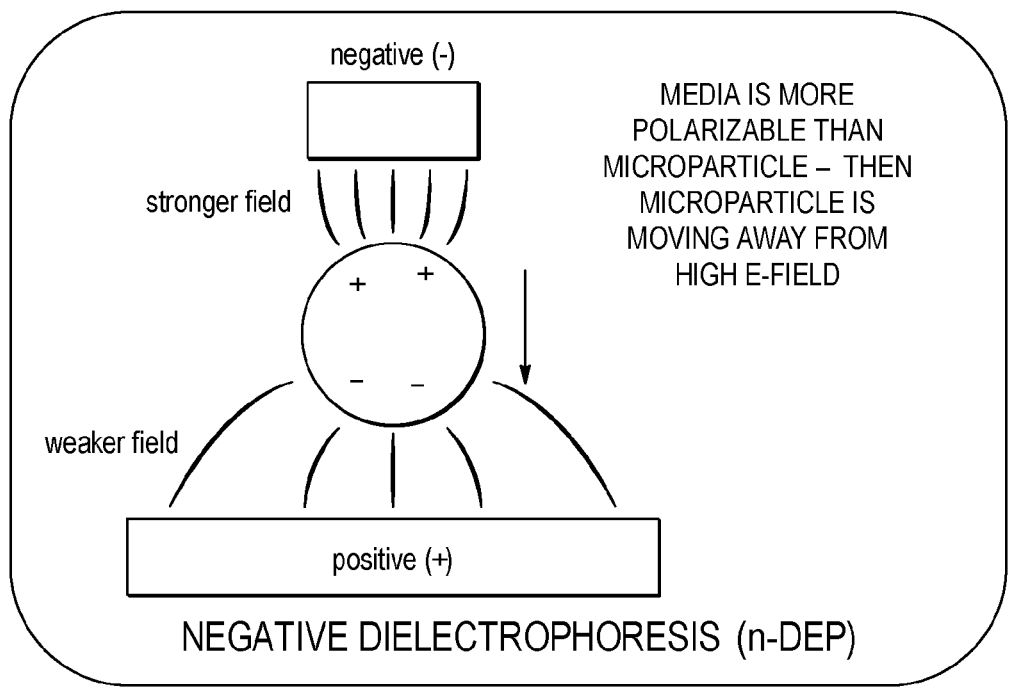
FIGS. 16A and 16B are diagrams illustrating particle motion principles employed by the present invention.
Figure 16B:
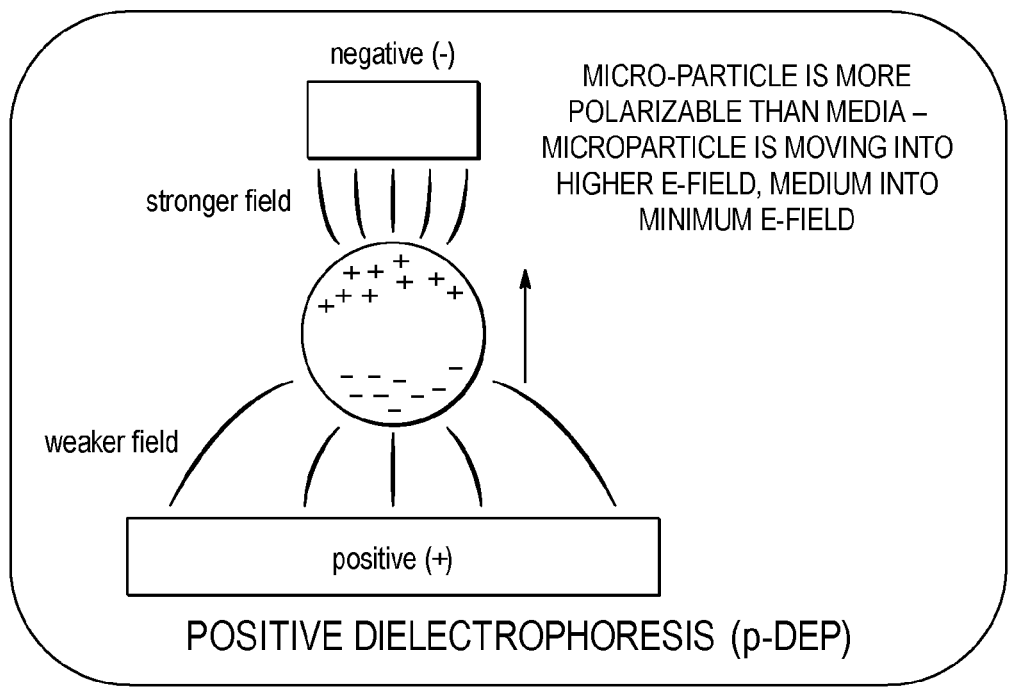

One or more nanometer scale objects, which may include any atoms, biological, geological, organic or inorganic molecules, proteins, antibodies, targets, polymer blocks, or other similar materials having a width dimension ranging from less than 100 nm to 50 µm, that generally develop dipole properties, but are referred to, for convenience, as nano-objects 28, may be suspended in the processing medium. Unlike charged particles, which can be caused to move by application of a uniform electric field, neutral dielectric objects will not similarly respond. Neutral dielectric particles suspended in or part of a medium will develop a dipole polarization when subjected to a uniform DC electric field, but the forces exerted on them will generally cancel. When the electric field is non-uniform, however, dielectrophoretic (DEP) motion occurs. On the other hand, as illustrated in FIG. 16A, in a non-uniform electric field, where the medium is more polorizable than a particle suspended in it, the particle moves, relative to the medium, away from the stronger electric field (called negative dielectrophoresis (n-DEP). And as illustrated in FIG. 16B, where the medium instead is less polorizable than the particle suspended in it, the particle moves, relative to the medium, toward the stronger electric field (called positive dielectrophoreses (p-DEP).

The dielectrophoretic force imposed on a dipolar object is also affected by the frequency or time rate of change of the electric field. Different rates affect the object differently. Elongated objects are affected differently than spherical objects by the electric field, and can be affected by uniform fields, where spherical objects generally are not. Electric fields can also affect the interaction of liquids with solids, modifying hydrophobic and hydrophilic properties, which is a factor in electrowetting on dielectrics. To deal with the complex interactions that determine final motions of these dipolar objects in these electric fields, the EFA embodiments of the present invention provide well developed, flexible platforms that are sophisticated enough to control objects in the micron and sub-micron range onto substrates in the centimeter range with reasonable repeatability, speed, and large scale manufacturing capability. Techniques used for E-field manipulation of charged particles are inadequate for these purposes.

A substrate 30 is supported on a substrate support 32 such that the substrate 30 is exposed to the processing space 24 and processing medium 26. While not required, one exemplary substrate 30 may be 300 mm in diameter with a thickness of about 800 μm or prefabricated wafer with thinned area(s) across it.

An electric field applicator (hereafter "EFA" 34) with associated bias connections 36 (also referred to as a distribution coupling unit), may be operatively coupled to the substrate 30, such as being coupled to the chamber wall 22 of the processing chamber 20 proximate the substrate support 32, in the substrate support 32, or on the substrate 30. The EFA 34, along with the bias connections 36, may be a permanent fixture coupled to the processing chamber 20 or releaseably coupled thereto for interchangeability for particular use and applications. The EFA 34, along with the bias connections 36, provide E-field control at the surface of the substrate 30. By way of the bias connections 36, an EFA 34 may be operatively coupled to a voltage generator 38 that is configured to generate an alternating current (AC) voltage having a selected waveform, or some other time-varying voltage that varies according to some selected bias algorithm. More voltage generators may be employed for applying more complex and sophisticated bias algorithms to the EFAs, for example, variable phase across different ones of the generators.

In another embodiment, E-field is controlled by digitally formed bias at the electrode. Such approaches provide increased flexibility in creating and changing bias algorithms through programming tools. Different electric field algorithms may be required for different specific process applications. A typical practical range for electric field strength is from $7 \times 10^3$ V/m up to $2 \times 10^5$ V/m, though the range is not limited to these values.

Figure 10:
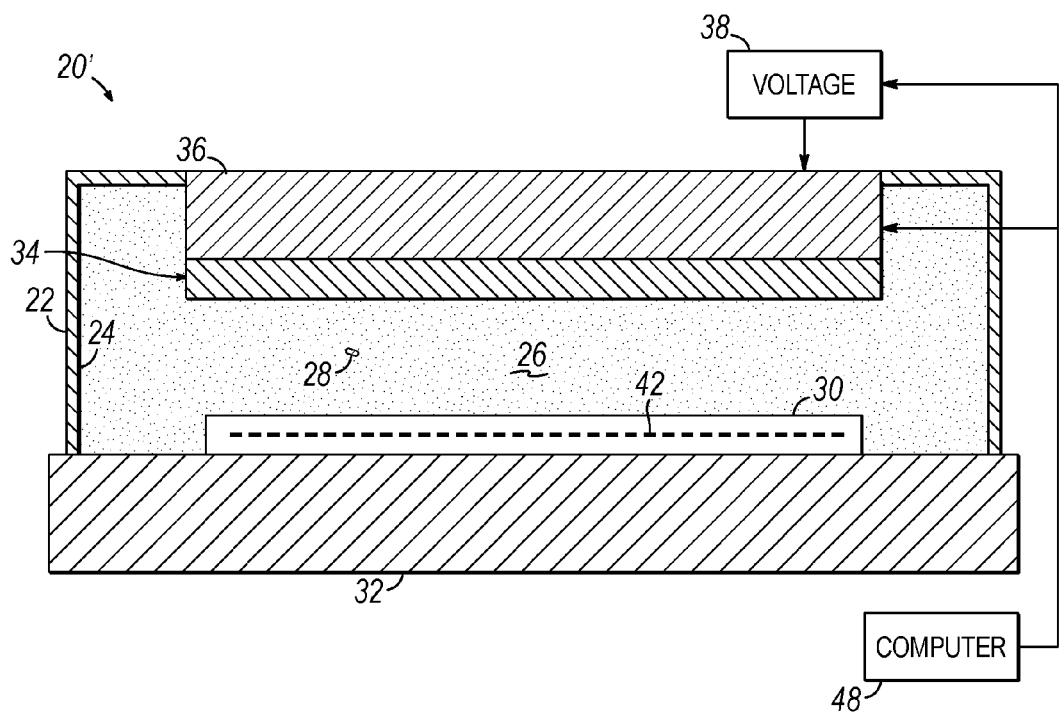
FIG. 10 is a schematic cross-sectional view, similar to FIG. 1, of a processing chamber having an electric field applicator in accordance with another embodiment of the present invention.

The processing chamber 20 of FIG. 1 has the E-field control at the bottom of the processing chamber 20. FIG. 10, as described below, depicts an alternative processing chamber 20' having the E-field control at the top of the processing chamber 20. FIGS. 15A-15E compare various modes of E-field control, including that for an alternative embodiment of the processing chamber 20', which has the E-field control distributed at both the top and bottom of the chamber, shown in FIGS. 15C-15E, or in other configurations in which multiple EFAs are used. Furthermore, EFAs configured for more or less permanent installation are provided with circuitry sufficiently sophisticated to individually bias different areas to produce field patterns described more fully below. On the other hand, externally mounted interchangeable EFAs can be in whole or in part hard wired to produce one or a limited number of patterns for the processing of a limited number of substrates, then exchanged with another EFA to produce field patterns suitable for processing another substrate.

In some embodiments, and as shown in FIG. 1, the processing chamber 20 may further include a radiation source 40 configured to provide in situ irradiation and/or post-radiation to the processing medium 26 and/or substrate 30. Additionally or alternatively, the substrate 30 may include an internal EFA 42 (shown in phantom) that is configured to be biased in a manner that is similar to the external EFA 34.

Figure 3A:
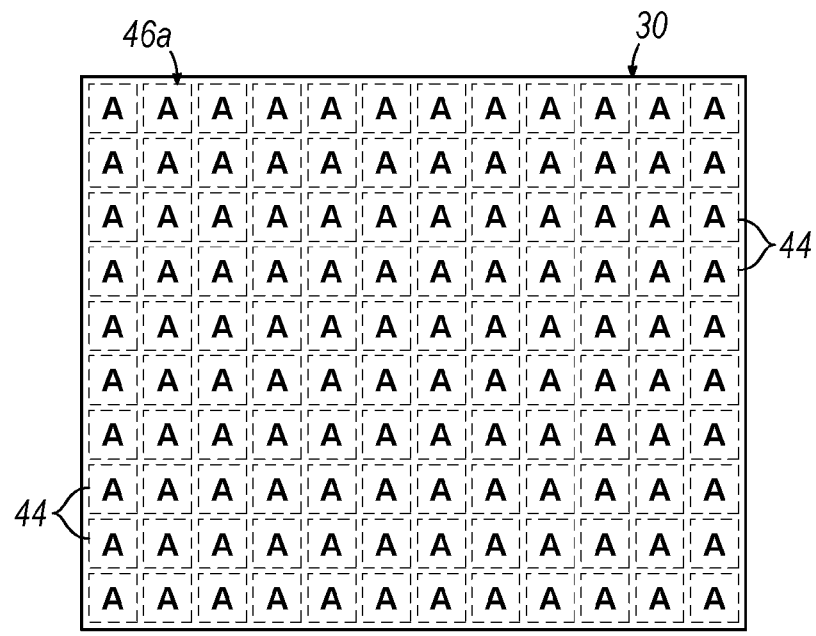
FIGS. 3A-3H are diagrammatic views of exemplary electric field zones generated by the electric field applicator within the processing chamber of FIG. 1.
Figure 3B:
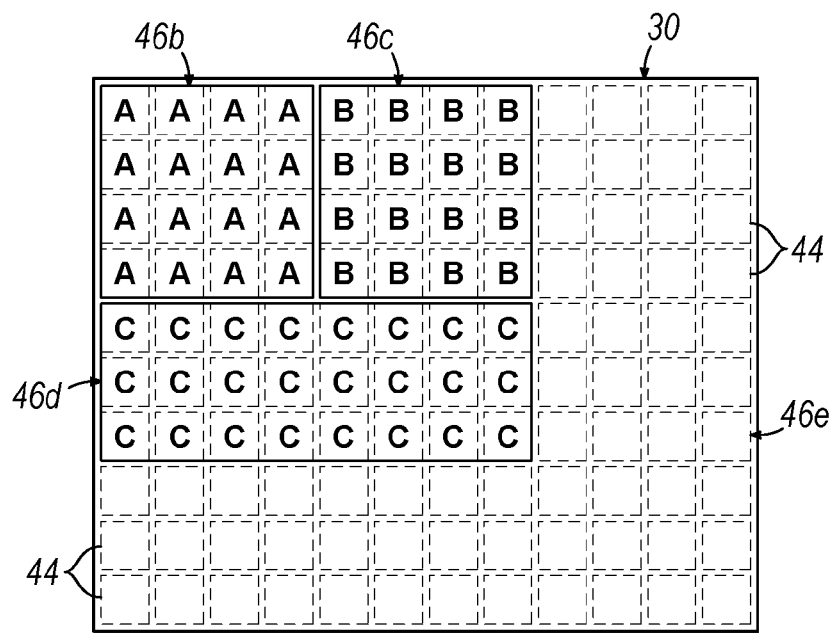
Figure 3C:
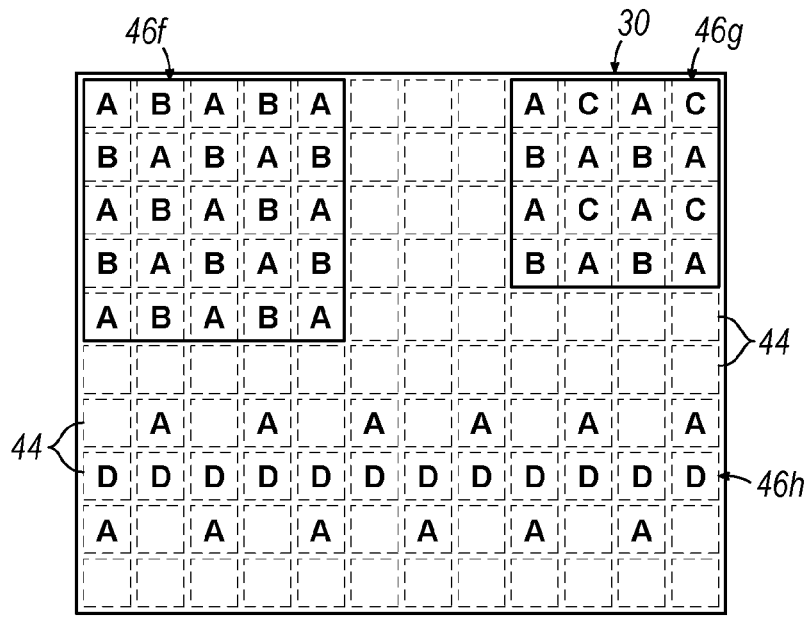

The EFA 34 (external as well as the internal) may, in typical embodiments, be generally planar, generally congruent to the size of the substrate 30, and may be operable to a plurality of zones 44, each zone 44 being an area in which the EFA 34 may generate a discrete force as compared to adjacent zones 44. Two or more adjacent zones 44 having the same bias algorithm to create a spatio-temporal electric field (generating the same force effect) define a subgroup (referenced generally as groups 46 and illustrated as subgroups 46a-46h in FIGS. 3A-3C). In FIG. 3A, all zones 44 have the same bias algorithm applied to form spatio-temporal distribution of the electric field, defining a single group 46a. FIG. 3B includes four subgroups: a first subgroup 46b comprising "A" spatio-temporal distribution of the electric field, a second subgroup 46c comprising "B" spatio-temporal distribution of the electric field, a third subgroup 46d comprising "C" spatio-temporal distribution of the electric field, and a fourth subgroup 46e comprising no applied electric field. However, subgroups need not be homogeneous; in fact, in FIG. 3C a first heterogeneous subgroup 46f of 5×5 zones includes an alternating sequence of "A" spatio-temporal distribution of the electric fields and "B" spatio-temporal distribution of the electric fields while a second heterogeneous subgroup of 4×4 zones alternates between alternating rows of "A" and "C" spatio-temporal distribution of the electric fields and "A" and "B" spatio-temporal distribution of the electric fields. Still other subgroups 46h need not be limited to a particular grid-like area. For example, the E-field control of the apparatus of the present invention is capable of providing the spatial distributions illustrated in FIGS. 3D-3H. As a result, a time dependent, macro-pattern 110a, 110b, 110c, 110d, 110e, 110f, may be generated. FIGS. 3D-3H illustrate macro-patterns in accordance with various embodiments of the present invention and in which open pixels indicate no voltage potential, darkened pixels indicate a positive voltage potential, and shaded pixels indicate a negative voltage potential. The macro-pattern 110a, 110b, 110c, 110d, 110e, 110f is operable to generate time-variant electric fields to manipulate cells according to a selected model by imposing a dielectrophoretic force. The cells accordingly move and align into an optimal position, bringing groups of cells into closer proximity, and resulting in faster agglomeration and adhesion to facilitate rapid growing of the tissue.

Figure 2:
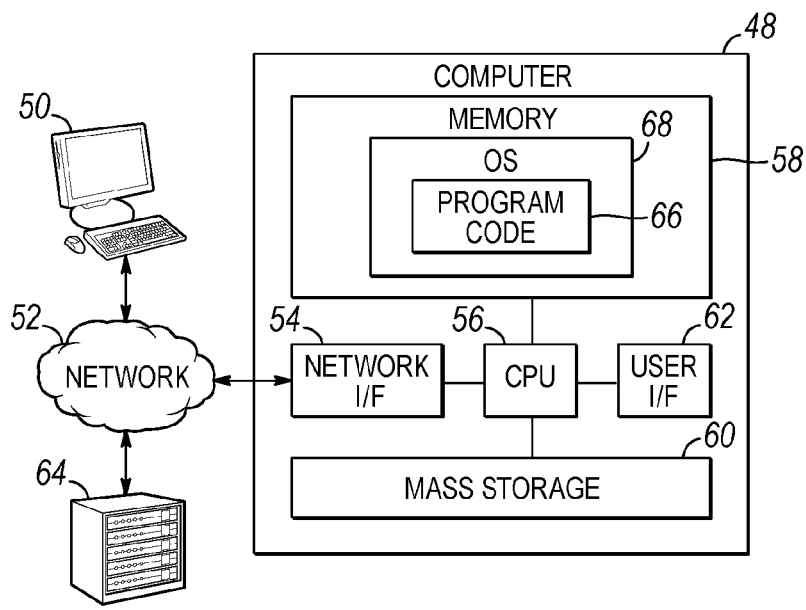
FIG. 2 is a diagrammatic view of a computer for use in controlling operation of the processing chamber of FIG. 1 and in accordance with embodiments of the present invention.

To generate the appropriate zones 44 and to effectuate the particular movement of nano-objects 28, one or more of the voltage generator 38, bias connections 36, EFA 34, internal EFA 42, and/or the radiation source 40 may be operatively coupled to a computer 48 that is configured to control operation thereof. FIG. 2 illustrates one computer 48 that may be considered to represent any type of computer, computer system, computing system, server, disk array, or programmable device such as multi-user computers, single-user computers, handheld devices, networked devices, or embedded devices, etc., suitable for use in accordance with embodiments of the present invention. The computer 48 may be implemented with one or more networked computers 50 using one or more networks 52, e.g., in a cluster or other distributed computing system through a network interface (illustrated as "NETWORK I/F" 54). The computer 48 will be referred to as "computer" for brevity's sake, although it should be appreciated that the term "computing system" may also include other suitable programmable electronic devices consistent with embodiments of the invention.

The computer 48 typically includes at least one processing unit (illustrated as "CPU" 56) coupled to a memory 58 along with several different types of peripheral devices, e.g., a mass storage device 60 with one or more databases, an input/output interface (illustrated as "I/O I/F" 62), and the Network I/F 54. The memory 58 may include dynamic random access memory ("DRAM"), static random access memory ("SRAM"), non-volatile random access memory ("NVRAM"), persistent memory, flash memory, at least one hard disk drive, and/or another digital storage medium. The mass storage device 60 is typically at least one hard disk drive and may be located externally to the computer 48, such as in a separate enclosure or in one or more networked computers 50, one or more networked storage devices (including, for example, a tape or optical drive), and/or one or more other networked devices (including, for example, a server 64 as illustrated herein).

The CPU 56 may be, in various embodiments, a single-thread, multi-threaded, multi-core, and/or multi-element processing unit (not shown) as is well known in the art. In alternative embodiments, the computer 48 may include a plurality of processing units that may include single-thread processing units, multi-threaded processing units, multi-core processing units, multi-element processing units, and/or combinations thereof as is well known in the art. Similarly, the memory 58 may include one or more levels of data, instruction, and/or combination caches, with caches serving the individual processing unit or multiple processing units (not shown) as is well known in the art.

The memory 58 of the computer 48 may include one or more applications (illustrated as "PROGRAM CODE" 66), or other software program, which are configured to execute in combination with the Operating System 68 and automatically perform tasks necessary for controlling the voltage generator 38, the bias connections 36, and/or the radiation source 40, with or without accessing further information or data from the database(s) of the mass storage device 60.

Those skilled in the art will recognize that the environment illustrated in FIG. 2 is not intended to limit the present invention. Indeed, those skilled in the art will recognize that other alternative hardware and/or software environments may be used without departing from the scope of the present invention.

Figure 4A:
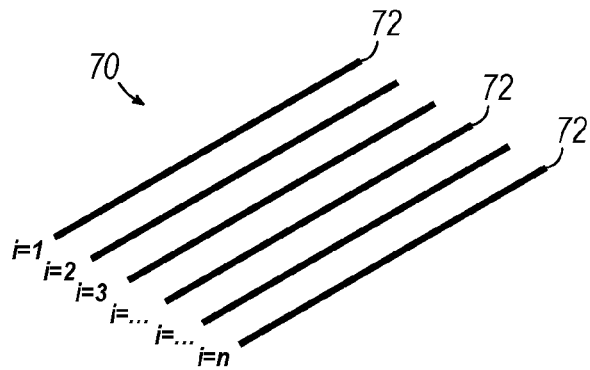
FIGS. 4A-4B are diagrams illustrating spatial bias functions of which the apparatus of the present invention is capable of producing.

Using the computer 48, the EFA 34 may be operated so as to provide a spatio-temporal distribution of the electric field over one or more zones 44 or subgroups 46 as desired. In that regard, the EFA 34 may comprise at least one grid member 70, a first embodiment of which is shown in FIG. 4A and includes a plurality of electrodes 72 arranged in a parallel array. Each electrode 72 may have a cross-sectional dimension ranging from about 0.1 mm$^2$ to about 1 mm$^2$ and is separated from an adjacent electrode 72 by distance that ranges from about 1 mm to about 50 mm. While the inter-electrode spacing of the grid member 70 as shown is constant, it would be readily appreciated that uneven spacing may also be used. The grid member 70 may be biased, as a whole, or subgroups thereof, by an output voltage from the voltage generator 38 (for example, 100 V peak-to-peak), at a particular phase offset and timing and in accordance with a selected waveform. The waveform may be generated by a function generator (not shown) or the computer 48 and, if necessary, the output voltage may be stepped using a transformer (not shown).

The applied voltage produces attractive or repulsive forces when electric field interacts with nano-objects in the form of a traveling wave on the surface of the substrate 30. Nano-objects 28 within the processing medium 26 and proximate the surface of the substrate 30 are influenced by the traveling wave and respond (e.g., align and/or travel) according to one or more electrokinetics principles, such as electrophoresis or dielectrophoresis. According to electrokinetics principles, a force (or torque) applied to the nano-object 28 is induced by the interaction of an induced dipole (due to polarization of the dielectric nano-object 28) with the imposed time-varying electric fields. When the electric field is uniform, an induced Coulombic attraction between accumulated charge of the nano-object 28 and the grid member 70 is cancelled (assuming symmetric distribution of the charge at a spherical nano-object) and the net force on the nano-object is zero. When the electric field is non-uniform, a resultant net force (i.e., non-zero) is induced and causes the nano-object 28 to undergo motion in dependence on the electric field configuration (translational motion, rotation, attraction, etc.). This latter effect occurs with AC or pulsed DC bias potentials and is known as dielectrophoresis, which is dependent on the applied frequency (ranging from about 100 Hz to about 100 MHz, more commonly in the 1 kHz to 10 kHz range). For nano-objects 28 that are in solution and have maximum width dimensions that are greater than 1 μm, dielectrophoretic behavior may be described by the Clausius-Mossotti factor model; nano-objects 28 in solution and having a maximum width dimension that is less than 1 μm exhibit greater surface charge effects such that an electrical double layer occurs and the nano-object's motion is more complex, due to the electric double layer and electro-osmotic transport.

By appropriately phasing the voltage potential of successive electrodes 72, for instance, in accordance with Equation 1, the traveling wave may be generated by in-phase and out-of-phase interferences and is effective to induce movement (rotational and/or translational) of the nano-objects 28.

$$V_i = V_0 \sin(\omega_i t + i\Delta\phi) \tag{1}$$

Figure 4B:
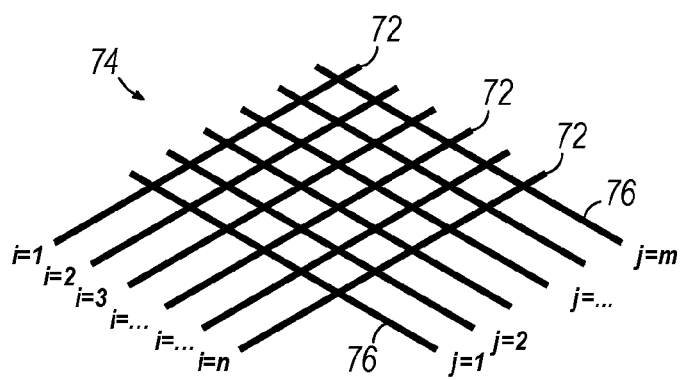
Figure 3D:
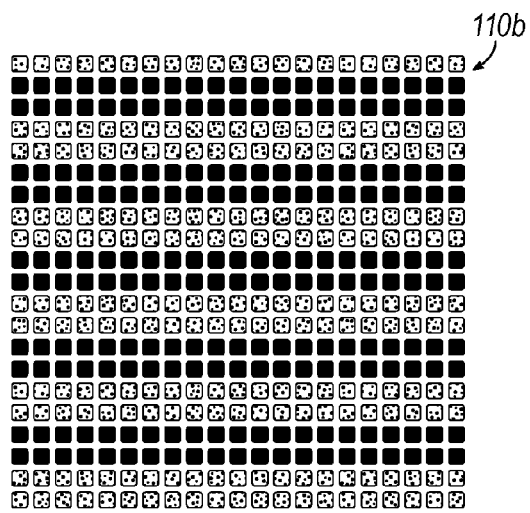
Figure 3E:
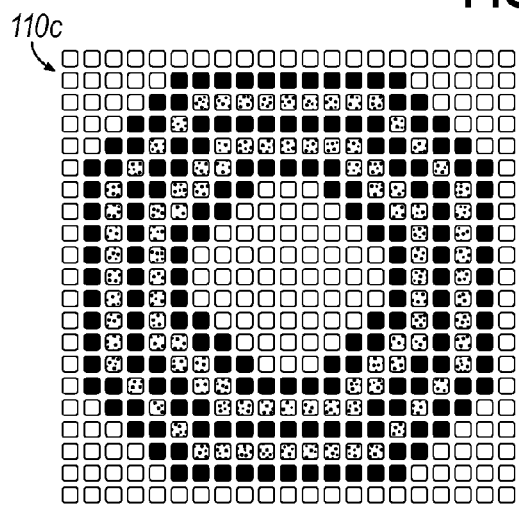
Figure 3F:
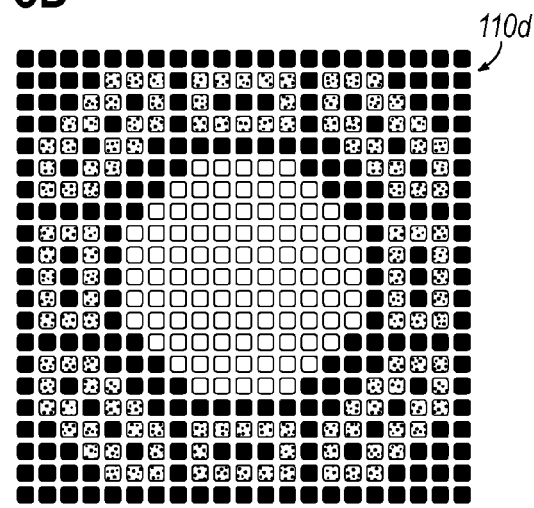
Figure 3G:
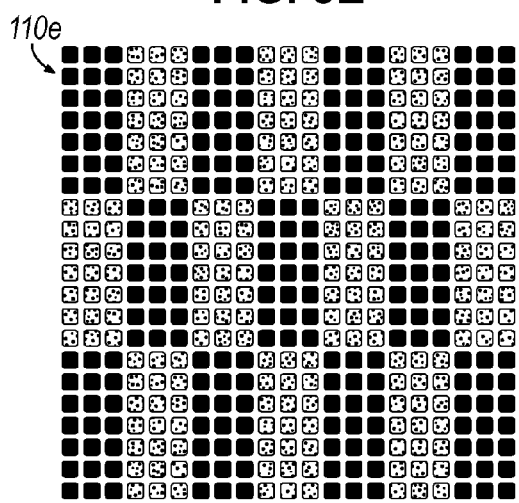
Figure 3H:
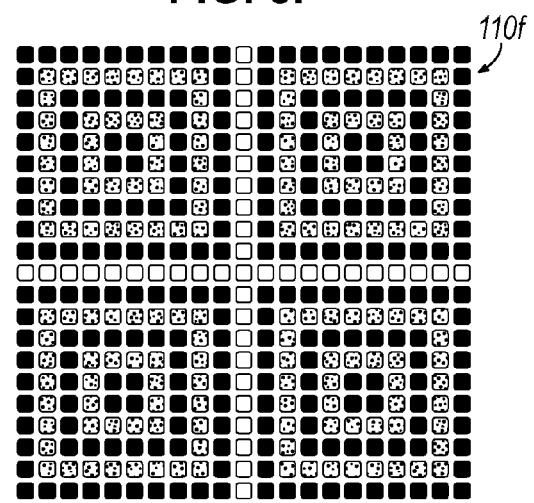

FIG. 4B illustrates a grid member 74 in accordance with another embodiment of the present invention that includes the electrodes 72 of FIG. 4A and a second plurality of electrodes 76, the electrodes 76 of the second plurality being aligned in a parallel array relative to itself and angularly oriented with respect to the first plurality of electrodes 72. The first plurality of electrodes 72 may be phase shifted in accordance with Equation 1 while the second plurality of electrodes 76 may be shifted in accordance with Equation 2.

$$V_j = V_0 \sin(\omega_j t + j\Delta\phi) \tag{2}$$

While the electrodes 72, 76 are shown to be generally orthogonal, the angular displacement between the first and second electrodes 72, 76 need not be so limited. Yet, the particular illustrative arrangement may provide a focusing effect when aligning or assembling nano-objects 28 into a point, a line, or other geometric design.

Figure 5A:
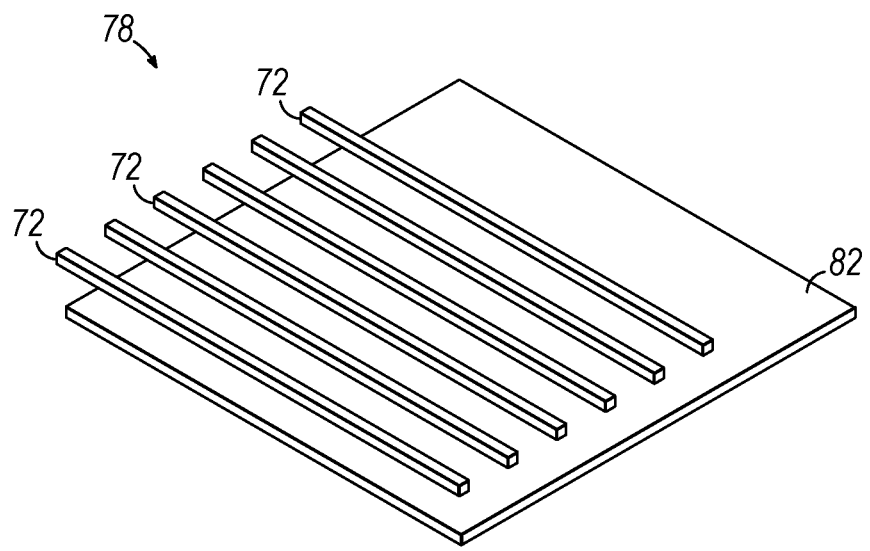
Figure 5B:
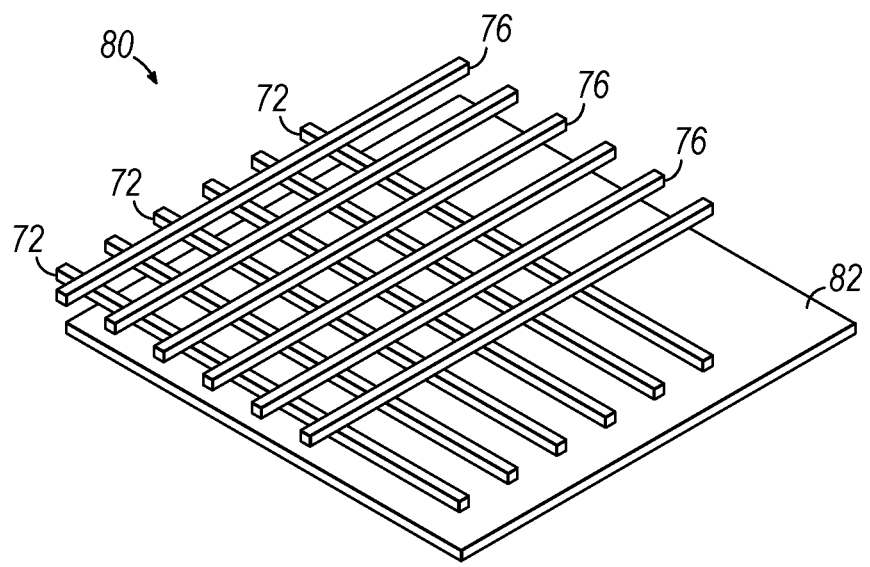

Grid members 78, 80, shown in FIGS. 5A and 5B respectively, are similar to the grid members 70, 74 of FIGS. 4A and 4B but further include an areal electrode 82 that is separated from other electrodes 72, 76 by a properly insulating layer (not shown). When an alternating or pulsing voltage potential is applied to the areal electrode 82, with or without phase shifted voltage potentials applied to the first and/or second electrodes 72, 76, the resultant electric field may provide agitating or mixing force configured to stir the nano-objects 28 within the processing medium 26. The areal electrode 82 may also be used in a manner to provide specific transport of the nano-objects 28 at the surface of the substrate 30.

Electrodes of a grid member comprising the EFA 34 need not be linear nor arranged into arrays. For example, in other embodiments of the present invention, the electrodes 84 may be oriented in a concentric-shaped grid member 88 as shown in FIG. 6A or electrodes 86 may be oriented in an axial or arcuate-shaped grid member 90 as shown in FIG. 6B. The concentric and axial electrodes 84, 86 may be used separately or in conjunction with other electrodes 72, 74, 82, including those described herein and may, in fact, be biased in accordance with Equation 1.

Still other grid members 92, 94 may include one or more interdigitated, planar electrodes 96, 98 as shown in FIG. 7 and in which the fingers 100, 102 of the electrodes 96, 98 are off-set and insulated to avoid electrical crossing. Electrodes 104, 106, 108, 110 of the grid member 94 shown in FIG. 8 are intertwining and again may be appropriately insulated.

Figure 9:
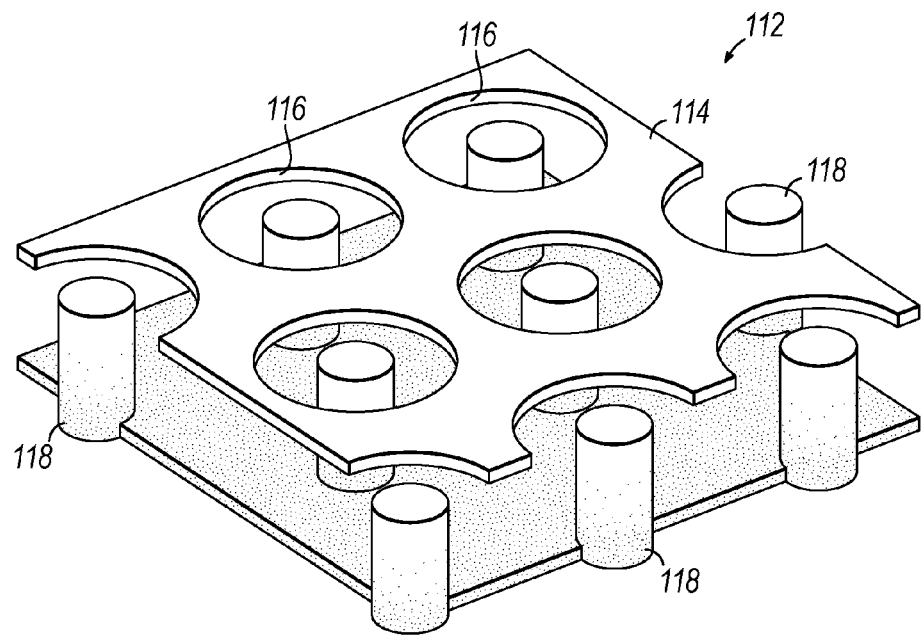

FIG. 9 illustrates another grid member 112 in accordance with still another embodiment of the present invention. The grid member 112 includes an areal electrode 114 with a plurality of openings 116 extending therethrough and in vertical alignment (i.e., interdigitated) with a corresponding plurality of post electrodes 118. Depending on the polarization ratio between the processing medium and the nano-object, this configuration will support increased densification of the nano-objects above the post electrodes 118, and slightly between them in the case of positive dipoles (DP). In the case of negative DPs, the depleted nano-object areas will be just above the post electrodes 118. The nano-objects will be forced into suspended positions above the substrate and will facilitate the forming of a specific structure. The actual effect will depend on geometrical relations in grid member 112. Implementing stabilization of such pre-structured nano-object distribution by proper radiation in specific media will generate a structurally or geometrically patterned chain structure on the surface of the substrate.

Figure 15A:
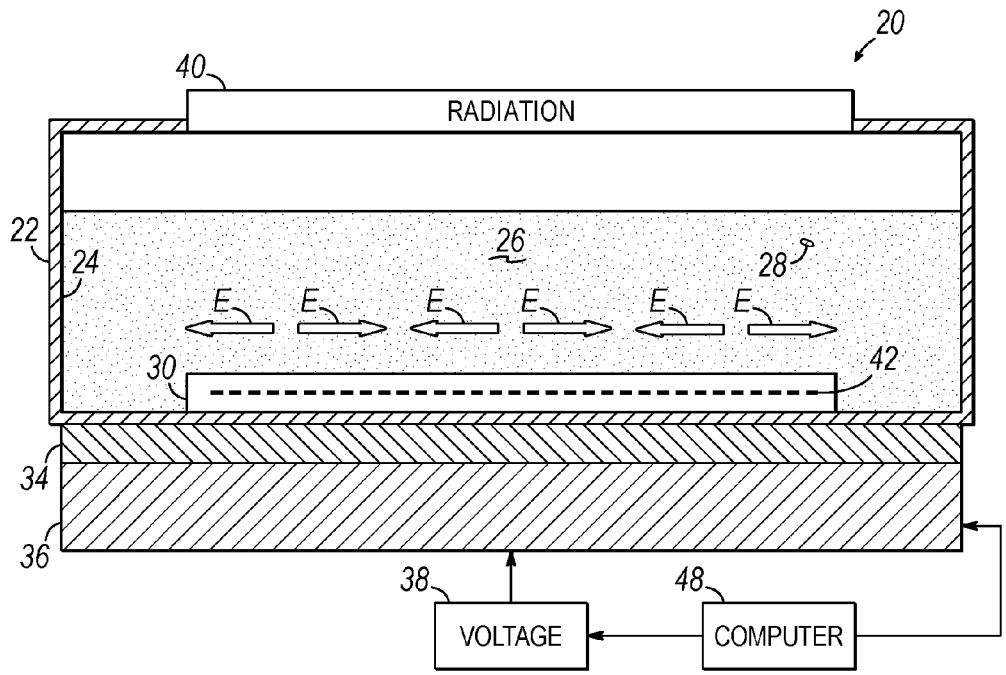
FIGS. 15A-15E are schematic cross-sectional diagrams, similar to FIGS. 1 and 10, of depicting processing chambers having electric field applicators in accordance with alternative embodiments of the present invention.
Figure 15B:
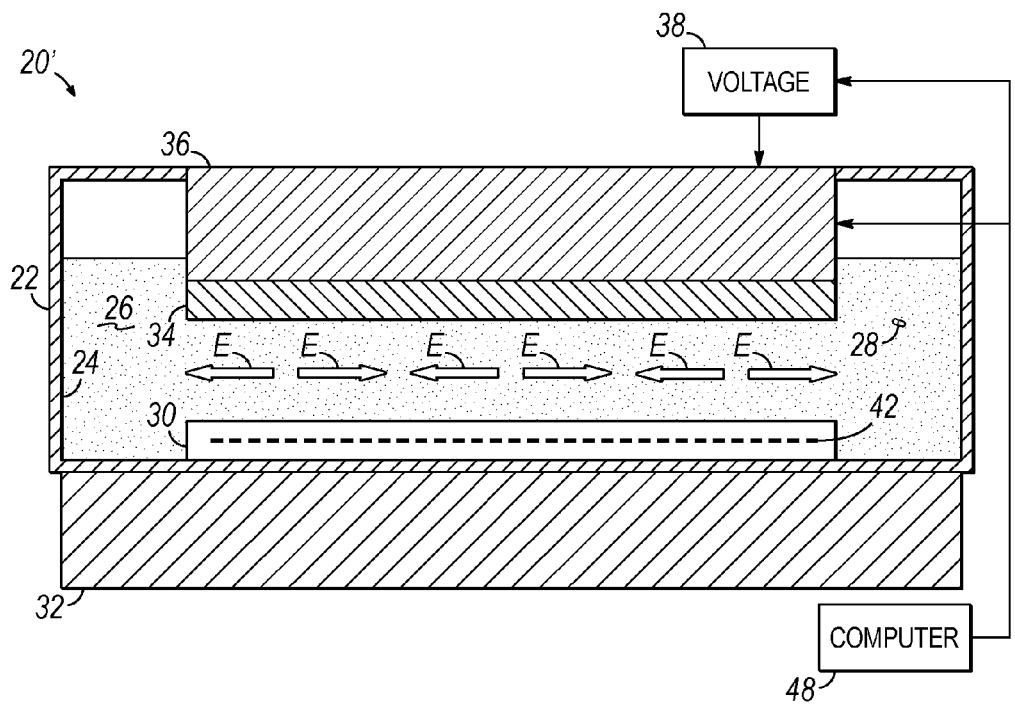

One of ordinary skill in the art with the benefit of the teachings herein would readily appreciate that the processing chamber need not be limited to the configuration shown in FIG. 1. In that regard, and as shown in FIG. 10, a processing chamber 20' in accordance with another embodiment of the present invention having particular applicability to thick substrates (for example, substrates 30 having a thickness greater than about 1 mm). The processing chamber 20' is similar to the processing chamber of FIG. 1 (like reference numerals referring to similar parts); however, the EFA 34 is positioned above the substrate 30 so as to apply the electric field from above the substrate 30. FIG. 15A shows the E-field control of the processing chamber 20 of FIG. 1 having a single or similarly configured EFAs at the bottom of the chamber, while FIG. 15B shows the E-field control of the processing chamber 20' of FIG. 10 having a single or similarly configured EFAs at the top of the chamber. Although not specifically shown herein, other processing chambers may be envisaged that incorporate the top and bottom approaches to the electric field applicator.

Figure 15C:
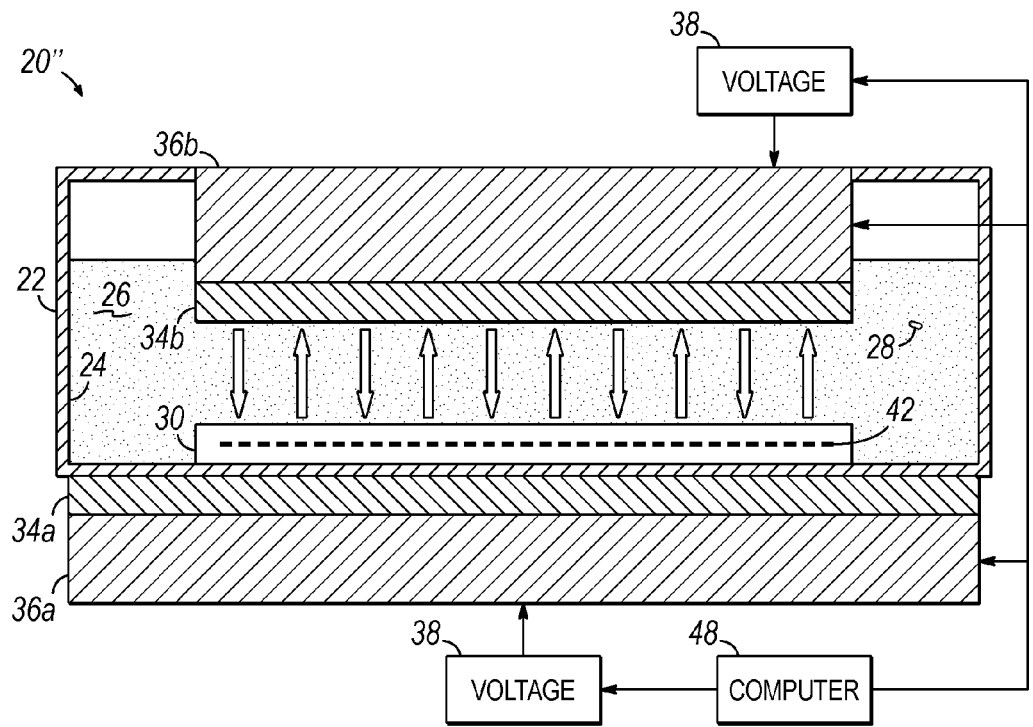
Figure 15D:
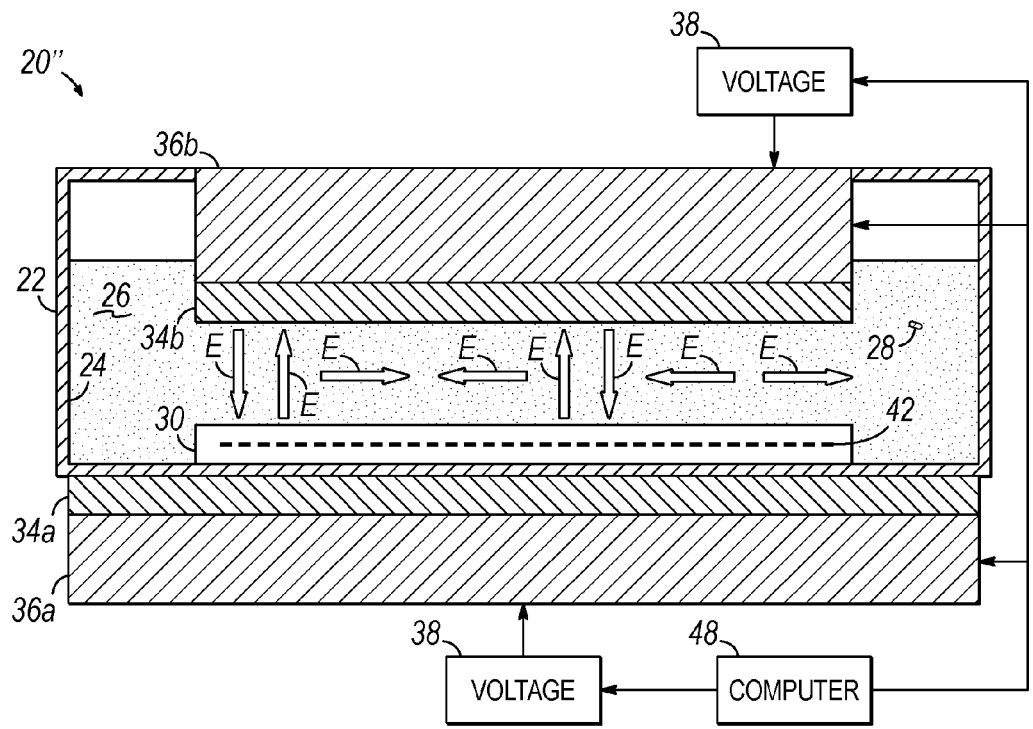
Figure 15E:
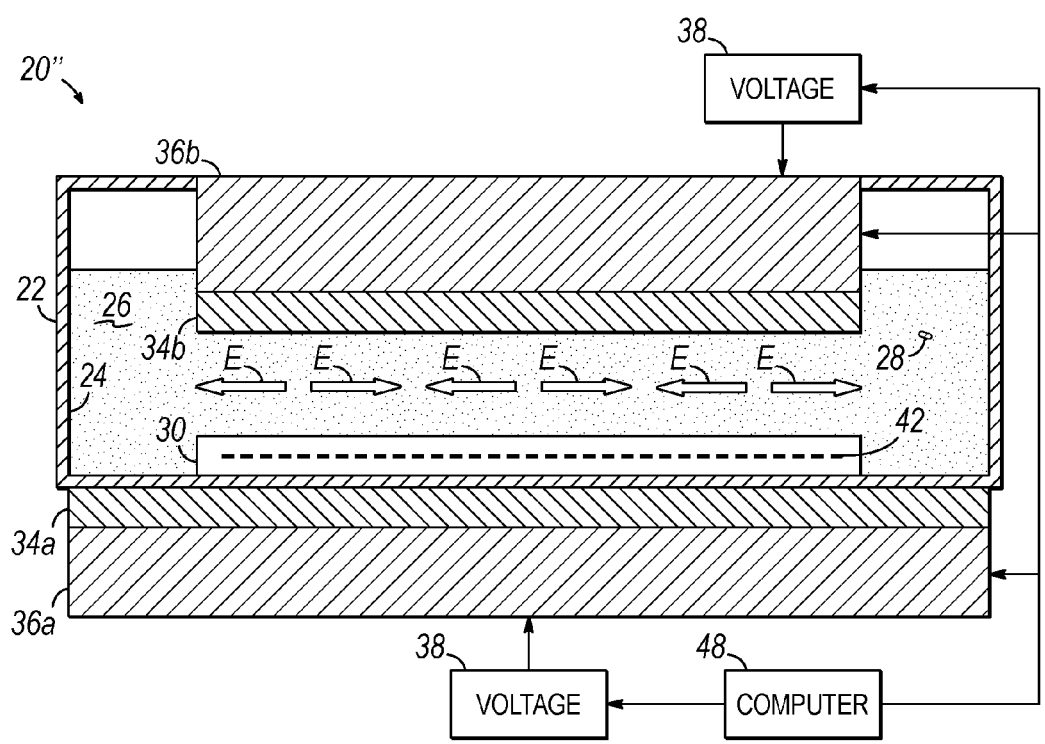

FIGS. 15A and 15B illustrate ways of controlling E-fields at the surface of a substrate with a single planar bias applied, showing the EFAs arranged as in the processing chamber of FIG. 1, at the bottom of the chamber, and FIG. 10, at the top of the chamber. FIGS. 15C-15E illustrate ways of controlling E-fields using multiple EFAs, preferably located at different levels or in different planes; those illustrated being depicted at the top and the bottom of the processing chamber 20'.

Figure 11:
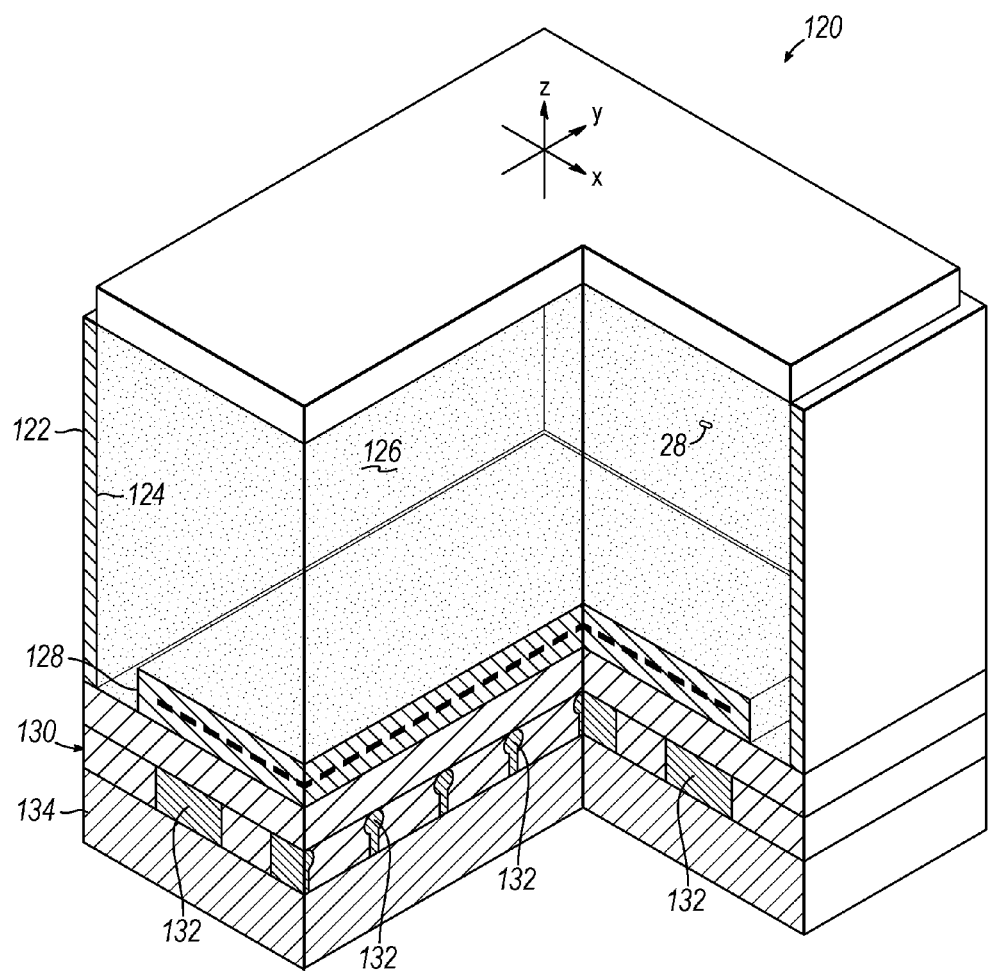
FIG. 11 is a schematic cross-sectional view of a processing chamber having an electric field applicator in accordance with one embodiment of the present invention.

FIG. 11 illustrates a processing chamber 120 in accordance with yet another embodiment of the present invention having a chamber wall 122 enclosing a processing space 124 containing a processing medium 126 with one or more nano-objects 28 therein. A substrate 128 is supported within the processing space 124 and exposed to the processing medium 126. The electrical field applicator 130 that is specifically shown herein includes a plurality of periodically arranged electrodes 132 with associated bias connections 134, is configured to generate an alternating current having a selected waveform, and may be operated in a manner similar to the processing chamber 20 of FIG. 1. The electrodes 132, having a selected geometric shape, are spaced in the y-axis direction in a periodic nature such that the distance between adjacent electrode members along the y-axis, $2d_{fy}$, ranges from about 50 µm to about 1 mm.

Figure 12A:
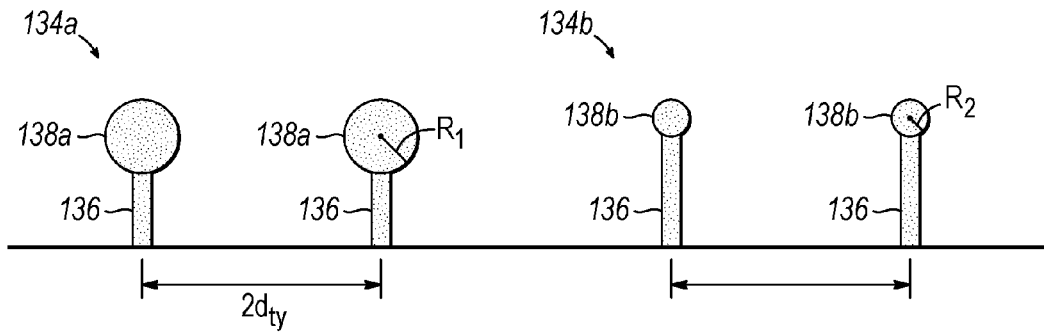
Figure 12B:
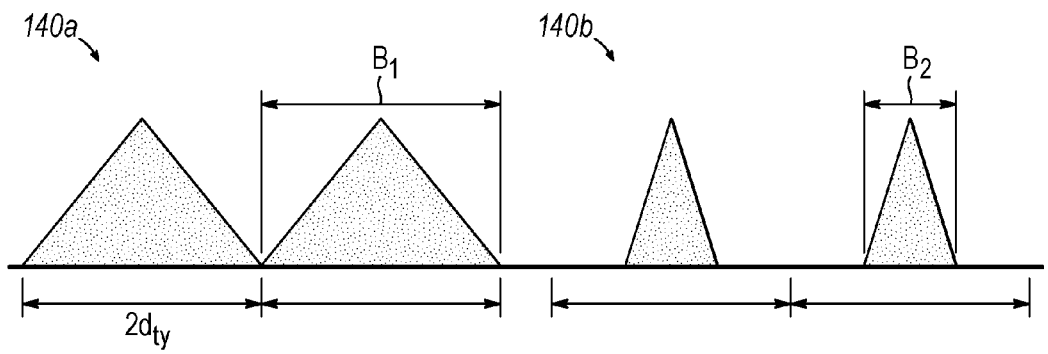
Figure 12C:
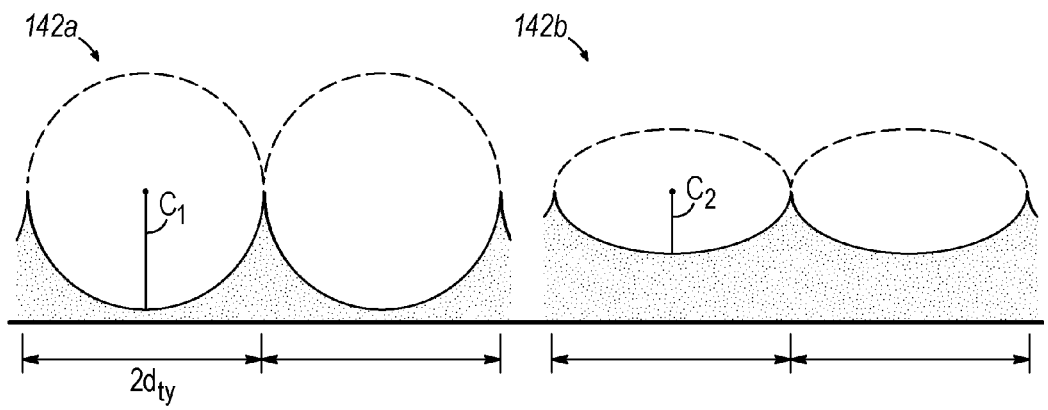

The shape and size of the electrodes may vary, a few examples of which are shown in FIGS. 12A-12C. FIG. 12A illustrates electrodes 134a, 134b having a stem 136 and a circular portion 138a, 138b of which the radius may be selected and for which the radius, $R_1$, of electrodes 134a is greater than the radius, $R_2$, of electrodes 134b and adjacent ones of the electrodes 134a, 134b are spaced with a periodicity, $2d_{fy}$, which may range from 50 µm to about 1 mm interelectrode distance. FIG. 12B illustrates pyramidal electrodes 140a, 140b, again spaced with selected periodicity, $2d_{fy}$, but with a base length varying such that the electrode 140a has a base length, $B_1$, greater than the base length, $B_2$, of the electrode 140b.

Yet another example, electrodes 142a, 142b may vary in concavity, such as $C_1$ and $C_2$ shown in FIG. 12C. The shape, size, and periodicity of the electrode may be selected on desired movement of the nano-objects 28 and the in-plane resolution of the zones 44 and thus should not be limited to the particular shapes, sizes, and configurations as shown herein.

Furthermore, and regardless of the particular electrode shape and size selected, the electrodes 134a may also be arranged linearly in the y-axis direction, as shown in FIG. 13A, or may also be offset in the x-axis direction, as shown in FIG. 13B. By off-setting the electrodes 134a, one or more groups of the electrodes 134a may be arranged, such as is shown in FIG. 14, each group being separately biased in a manner similar to the electrodes 72, 76 (FIG. 4B) above, so as to define the zones 44 (FIG. 3A) with a selected spatial resolution.

While the term "nano-objects" has been defined more broadly above to apply to multi-micron sized objects, object size smaller than 100 nm is suitable for most semiconductor applications of the invention. Semiconductor applications of the invention include, for example, cleaning a wafer, e.g., to locally force flow of a liquid or other fluid in a cleaning process. Another semiconductor application of the invention is applying fluid agitation, for example, ultrasonic agitation, to a cleaning fluid or other medium. The nano-objects may, in such cases, be the molecules of such fluids. Further, a time varying change in a field gradient may be applied to move particles (considered as "nano-objects") from the semiconductor substrate into the fluid.

In general, as explained above, the time-varying change in electric field can be AC. Where DC is applied, at least temporarily, particles tend to move toward an electrode or one of the areas of a given potential bias. In general, where the particles are more polarizable than the medium, they move toward the higher E-field, but where the medium is more polarizable than the particle, the particles move toward the weaker E-field. With AC, for example, simple sinusoidal AC, particles can be made to collect between such electrodes. The time varying function to use for various purposes depends on the physical and electrical properties of the particle or nano-object, as well as to the properties of the medium (the viscosity or electrical properties of the medium, for example). In various plasma assisted coating or etching processes in semiconductor manufacture, the present invention is useful for controlling charged particles, such as by moving ions to the surface of a substrate, etc. The concept can be used in deposition to change deposition rates in local areas of a semiconductor substrate. In structures with areas of high electric field concentrations, such as around corners or features of varying geometry or conductivity, the invention can be used to even out the electric field on the substrate.

Further applications of the invention to semiconductor manufacture include "self-assembly" and surface preparation for grid structure, moving polymers into a lower energy state, changing critical dimensions, electrically charging during etching, etc.

The invention can be used to transport particles in a highly viscous fluid, such as a hydrogel, which can be highly viscous. For example, it can be used to first move one type of particle, then different types of particles, selecting the voltage and timing or special configuration of the areas to facilitate particle selection. Or, it can be used to affect motion of a fluid, or to manipulate a medium. Primarily, selective motion of different particles or media can be done sequentially, but it can be done simultaneously by application of different signals, although this would make the apparatus and its control more complex. There can be more than one grid or one grid with more than one field pattern applied. The time varying factor can be in the form of DC switching, on and off, at, for example, 100 s or 1000 s of Hz, as well as a continuous waveform.

Figure 2A:
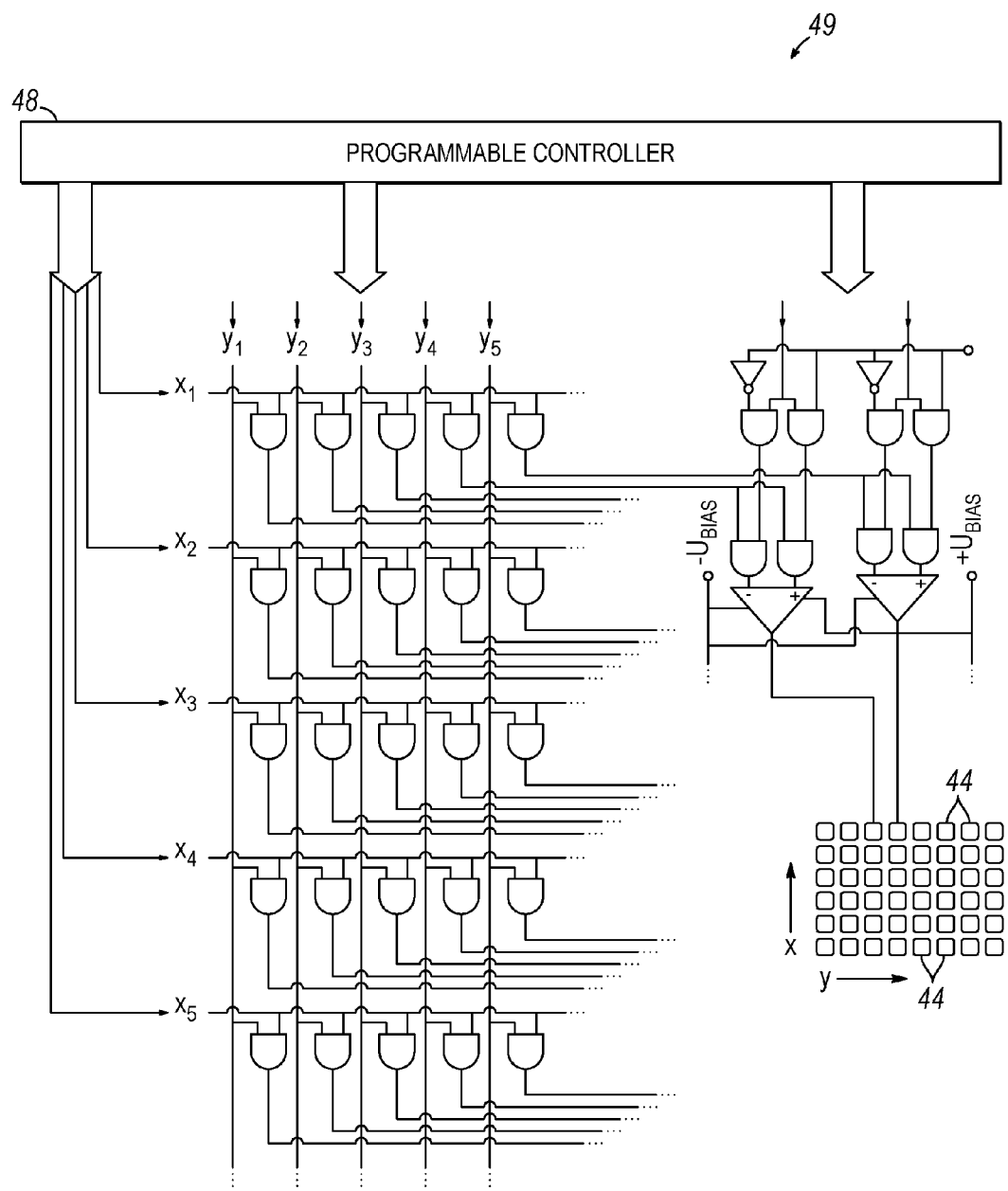
FIG. 2A is a logic diagram of an embodiment circuitry for biasing the electric field applicator of the apparatus of FIG. 1.

The circuits needed to apply potential to a grid are known technology. Several of the known schemes used to energize pixels on a display may be used to apply potentials to the areas. For example, the electrodes of the EFA 34 may be selectively operable to define a plurality of zones 44 by circuitry 49 as diagrammatically illustrated in FIG. 2A. The circuitry 49 may include a programmable controller, which may be in the form of a computer 48. Each zone 44 may be an individual electrode or an area influenced by several electrodes in which a discrete force may be applied to a particle and/or the medium. If desired, two or more adjacent zones 44 having the same (homogeneous) or different (heterogeneous) electric fields may define a subgroup that is operable to generate a selected force onto the particles. By specifying the function to be achieved, an electrical design engineer would be able to provide the appropriate logic. Therefore such control schemes are not described here in detail.

Other structural details and alternatives to the processing apparatus of this invention and other applications of the general concepts set forth herein are set forth in the related and commonly assigned International Application Serial No. PCT/US2012/049056 entitled SYSTEM AND METHOD FOR TISSUE CONSTRUCTION USING AN ELECTRIC FIELD APPLICATOR filed on even date herewith by the inventor hereof, hereby expressly incorporated herein by reference. This international application describes use of the present invention in the construction of tissue in which individual cells in the range of 1 to 10 microns in size, or clusters of cells that make up the particles or objects of interest in the 50-100 micron size range.

The temporal or time-varying factor refers to changes of a short term nature. For example, while layers of cells are processed with grids changed from layer to layer or within a layer, it is during the application of a layer in which potentials are temporally varied to move or orient cells or cell clusters, or to control charge build up in one layer during its construction and before going to another layer. In tissue construction, for example, field strength must be limited to prevent damage to the tissue.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be made from such details without departing from the scope of the general inventive concept.

What is claimed is:

1. A method of electric field processing, comprising:
providing an electric field processing apparatus comprising: a processing chamber configured to receive a substrate and a processing medium having dielectric properties affected by an electric field, at least one electric field applicator, and a distribution coupling unit for coupling an electrical bias to the at least one electric field applicator, wherein the at least one electric field applicator includes at least one electric field applicator directly coupled to the processing chamber;
supporting in the processing chamber a substrate to be processed;
introducing a processing medium into the processing chamber;
applying a non-uniform, time-varying electrical bias to the at least one electric field applicator to create an electric field to exert a dipolar effect on the processing medium in the vicinity of or at the surface of the substrate or both; and
processing the substrate with the effected processing medium.

2. The method of claim 1 wherein:
the processing of the substrate includes constructing one or more layers on the substrate.

3. The method of claim 1 or 2 wherein:
the processing medium includes neutral dielectric particles.

4. The method of any of claims 1 to 3, further comprising:
irradiating the substrate with at least one of microwave radiation, ultraviolet radiation, or infrared radiation.

5. The method of any of claims 1 to 3, further comprising:
depositing or modifying a layer on the substrate with filament-assisted chemical vapor deposition (FACVD), initiated chemical vapor deposition (iCVD), or both.

6. The method of any of claims 1 to 5, wherein the processing medium and electrical bias are selected to prepare at least one layer on the substrate for bonding the substrate to a second substrate.

7. The method of any of claims 1 to 6, wherein the processing medium and electrical bias are selected to deposit carbon nanotubes (CNTs) with a controlled orientation, on the substrate.

8. The method of any of claims 1 to 7, wherein the processing medium and electrical bias are selected to affect the structure, or orientation, or both, of a first deposited layer on the substrate.

9. The method of claim 8, wherein a second electrical bias is applied to the at least one electric field applicator to create a second electric field to affect the structure, or orientation, or both, of a second deposited layer on the substrate.

10. The method of any of claims 1 to 9, wherein the processing medium contains suspended particles and the time-varying electrical bias is selected to generate an electric field that affects the motion of the suspended particles in the processing medium.

11. The method of claim 10, wherein the motion of the suspended particles induces bulk motion of the processing medium.

12. The method of claim 11, wherein the motion of the suspended particles causes suspended particles of different properties to follow different paths in the processing medium, thereby causing the suspended particles to be sorted.

13. The method of any of claims 10 to 12, wherein the suspended particles are bioagents, and the motion of the suspended particles is controlled by applying the time-varying electrical bias so as to deposit the suspended particles at predetermined locations on the substrate.

14. The method of claim 1, wherein the at least one electric field applicator directly coupled to the processing chamber includes a bottom electric field applicator coupled outside of the processing chamber beneath the substrate.

15. The method of any of claims 1 to 6, wherein the substrate is a semiconductor wafer.

16. The method of claim 15 wherein the processing includes etching material on the semiconductor wafer.

17. The method of claim 15 or 16 wherein the processing includes depositing a film on the semiconductor wafer.

18. The method of claim 14, wherein the at least one electric field applicator coupled to the processing chamber includes a top electric field applicator directly coupled to the processing chamber above the substrate.

19. The method of claim 18, wherein the at least one electric field applicator includes an internal electric field applicator coupled to the substrate.

20. The method of claim 18, wherein applying the electrical bias to create an electric field includes creating first electric field components lateral to the surface of the substrate and second electric field components normal to the surface of the substrate.

21. The method of claim 1, wherein the at least one electric field applicator coupled to the processing chamber includes a top electric field applicator directly coupled to the processing chamber above the substrate.

22. The method of claim 1, wherein applying the electrical bias to create an electric field includes creating first electric field components lateral to the surface of the substrate and second electric field components normal to the surface of the substrate.

23. The method of claim 1, wherein applying the electrical bias to create an electric field includes creating electric field components lateral to the surface of the substrate.

24. The method of claim 1, wherein applying the electrical bias to create an electric field includes creating electric field components normal to the surface of the substrate.

25. The method of claim 1, wherein the at least one electric field applicator includes an internal electric field applicator coupled to the substrate.

26. The method of claim 1, wherein the processing medium is a gas.

27. The method of claim 1, wherein the processing medium is a liquid.

28. The method of claim 1, wherein the at least one electric field applicator directly coupled to the processing chamber is interchangeable, the method comprising:

selecting the at least one electric field applicator configured to produce a target pattern for the electric field for use with the specific substrate to be processed and directly coupling the selected at least one electric field applicator to the processing chamber prior to introducing the processing medium.

29. The method of claim 1, wherein the at least one electric field applicator is of a size substantially equal to the size of the substrate.

30. The method of claim 1, wherein the at least one electric field applicator is of a size smaller than the size of the substrate, and wherein the applying includes scanning the at least one electric field applicator across the substrate.

31. The method of claim 1, wherein applying the electrical bias includes applying a DC potential.

32. The method of claim 1, wherein applying the electrical bias includes applying an AC or RF potential.

33. The method of claim 1, wherein the electrical bias applied to the at least one electric field applicator is applied by direct electrical contact with the distribution coupling unit.

34. The method of claim 1, wherein the electrical bias applied to the at least one electric field applicator is applied by inductive coupling with the distribution coupling unit.

35. The method of claim 1, wherein the electrical bias applied to the at least one electric field applicator is applied by capacitive coupling with the distribution coupling unit.

* * * * *

UNITED STATES PATENT AND TRADEMARK OFFICE
CERTIFICATE OF CORRECTION

Page 1 of 1

PATENT NO.      : 8,916,055 B2
APPLICATION NO. : 13/823690
DATED           : December 23, 2014
INVENTOR(S)     : Jozef Brcka et al.

It is certified that error appears in the above-identified patent and that said Letters Patent is hereby corrected as shown below:

In the Specification

In Col. 1, lines 18-19, "by the inventor hereof," should read --by an inventor hereof,--.

In Col. 4, line 36, "FIGS. 1 and 10, of depicting processing chambers" should read --FIGS. 1 and 10, depicting processing chambers--.

In Col. 9, line 58, "chamber 20′ in accordance" should read --chamber 20′ is provided in accordance--.

In Col. 11, line 46, "100 s or 1000 s of Hz," should read --100s or 1000s of Hz,--.

In Col. 12, lines 4-5, "by the inventor hereof," should read --by an inventor hereof,--.

In Col. 12, lines 7-8, "tissue in which individual cells" should read --tissue having individual cells--.

Signed and Sealed this
Ninth Day of June, 2015

Michelle K. Lee
*Director of the United States Patent and Trademark Office*